(12) United States Patent
Meyer-Ingold

(10) Patent No.: US 8,258,365 B2
(45) Date of Patent: Sep. 4, 2012

(54) ACRYLATE ADHESIVE COMPOSITION WITH WATER-RESISTANT ADHESIVE PROPERTIES

(75) Inventor: Wolfgang Meyer-Ingold, Hamburg (DE)

(73) Assignee: Beiersdorf AG, Hamburg (DE)

( * ) Notice: Subject to any disclaimer, the term of this patent is extended or adjusted under 35 U.S.C. 154(b) by 997 days.

(21) Appl. No.: 12/096,204

(22) PCT Filed: Sep. 28, 2006

(86) PCT No.: PCT/EP2006/066835
§ 371 (c)(1),
(2), (4) Date: Sep. 12, 2008

(87) PCT Pub. No.: WO2007/065742
PCT Pub. Date: Jun. 14, 2007

(65) Prior Publication Data
US 2009/0163845 A1 Jun. 25, 2009

(30) Foreign Application Priority Data

Dec. 8, 2005 (DE) .......................... 10 2005 059 058

(51) Int. Cl.
*A61F 13/00* (2006.01)

(52) U.S. Cl. ........................................... 602/41; 602/54

(58) Field of Classification Search .................... 602/41, 602/52, 54; 523/111, 120; 156/292, 327
See application file for complete search history.

(56) References Cited

U.S. PATENT DOCUMENTS

| 4,269,747 A | 5/1981 | Wada et al. |
| 5,302,629 A * | 4/1994 | Berejka .......................... 523/111 |
| 5,876,855 A | 3/1999 | Wong et al. |
| 5,925,417 A | 7/1999 | Fousse |
| 6,551,704 B2 | 4/2003 | Himmelsbach et al. |
| 6,860,961 B2 * | 3/2005 | Gibes et al. .................... 156/292 |
| 7,858,679 B2 * | 12/2010 | Messersmith et al. .......... 524/17 |
| 2003/0087338 A1 | 5/2003 | Messersmith et al. |

FOREIGN PATENT DOCUMENTS

| DE | 42 22 334 | 1/1994 |
| DE | 196 31 422 | 2/1998 |
| EP | 0 352 901 | 1/1990 |
| EP | 0 507 160 | 10/1992 |
| JP | 0 238 863 | 9/1987 |
| JP | 4-178323 | 6/1992 |
| JP | 10-60677 | 3/1998 |
| JP | 10-152662 | 6/1998 |
| JP | 11-228340 | 8/1999 |
| WO | 96/25469 | 8/1996 |
| WO | 97/23577 | 7/1997 |

OTHER PUBLICATIONS

Lee et al., "Synthesis of 3,4-Dihydroxyphenylalanine (DOPA) Containing Monomers and their Co-polymerization with PEG-diacrylate to Form Hydrogels," Journal of Biomaterials Science, Polymer Edition, vol. 15, No. 4, pp. 449-464 (2004).
Dalsin et al., "Bioinspired Antifouling Polymers," Materials Today, Elsevier Science, vol. 8, No. 9, pp. 38-46 (2005).
English Language Abstract of JP10-152662.
English Language Abstract of DE 42 22 334.
English Language Abstract of JP 11-228340.
English Language Abstract of JP 4-178323.
Waite, "Evidence for a Repeating 3,4-Dihydroxyphenylalanine- and Hydroxyproline-containing Decapeptide in the Adhesive Protein of the Mussel, *Mytilus edulis* L.," The Journal of Biological Chemistry, vol. 258, No. 5, pp. 2911-2915 (1983).
Yu et al., "Role of L-3,4-Dihydroxyphenylalanine in Mussel Adhesive Proteins," The Journal of the American Chemical Society, vol. 121, pp. 5825-5826 (1999).

* cited by examiner

*Primary Examiner* — Michael A. Brown
(74) *Attorney, Agent, or Firm* — Abel Law Group, LLP

(57) ABSTRACT

Acrylate adhesive composition comprising N-methacryloyl-3,4-dihydroxyphenylalanine and/or N-acrylol-3,4-dihydroxyphenylalanine. The adhesive composition ensures an adhesion of substrates under moist conditions, in particular a biocompatible and waterproof adhesion to human skin.

13 Claims, No Drawings

ACRYLATE ADHESIVE COMPOSITION WITH WATER-RESISTANT ADHESIVE PROPERTIES

BACKGROUND OF THE INVENTION

1. Field of the Invention

The invention comprises to an acrylate adhesive composition and plasters or dressings containing same, the adhesive strength of which composition does not sustain any losses even under humid conditions.

2. Discussion of Background Information

Adhesive compositions have a broad range of uses in the production of wound treatment products, if they contain only minimal amounts of residual monomers due to a high degree of polymerization and can thus be considered to be particularly well tolerated by the skin.

A number of printed publications in this respect disclose various acrylate compositions and rubber pastes, such as, e.g., EP 352901, EP 238863, JP 1060677, U.S. Pat. No. 4,269,747, U.S. Pat. No. 5,876,855, JP 10152662, DE 42 22 334, DE 196 31 422, DE 102 13 759, WO 9625469 or WO 9723577. The production of polymer matrices, in particular gel matrices, from polyacrylates has been known for many years and is described, e.g., in EP 0 507 160, JP 11-228340 and JP 04178323.

The main object of the adhesive compositions used is thereby a secure adhesion of the wound treatment product to the skin and an easy and in particular pain-free removal from the skin at the end of the application period.

However, this most important property of a plaster, which is also repeatedly cited in consumer polls, cannot be achieved in every case. Depending on the liquid absorption capacity of the wound dressing and/or the adhesive composition as well as on the water-vapor permeability of the plaster, perspiration or sweating lead to more or less frequent undesirable detachment of plasters.

In the prior art there has been no lack of attempts to master these disadvantages and to develop an improved, less moisture-sensitive adhesive composition, such as, e.g., through the additional use of superabsorbents or through hydrophilization.

For acrylate adhesive compositions the use of hydroxyethyl acrylate or hydroxyethyl methacrylate for hydrophilization is described, e.g., in U.S. Pat. No. 5,302,629.

Adhesive compositions based on synthetic rubber can be hydrophilized by the addition of a so-called surfactant, as described in U.S. Pat. No. 6,860,961.

Another problem in the cross-linking of polyacrylic acid to form a self-adhesive matrix or gel is that a matrix once produced with defined physical properties, viscosity, adhesiveness, etc. must have the same defined properties in a later production process. This reproducibility is expensive to realize or cannot be realized at all with the cross-linking technologies currently known.

It is known from a completely different technical field that, e.g., barnacles and mussels can achieve a perfect waterproof adhesion. 3,4-Dihydroxyphenylalanine (DOPA) thereby plays an important role, after repetitive sequences of DOPA-containing decapeptides have been identified in the protein that has proven to be responsible for the adhesion, as stated in the literature (J. H. Waite, J. Biol. Chem. 258, 2911-2915 [1983]). The mechanism of the sticking and the firm adhesion then occurring of these organisms via so-called MAPs ("Mussel Adhesive Proteins") has also been explained (M. Yu et al., J. Am. Chem. Soc. 121, 5825-5826 [1999]).

After the so-called mussel adhesive has been identified, it was possible according to US 20030087338 to incorporate this principle into synthetic polymers. In US 20030087338 this principle is based on the chemically synthesized L-3,4-dihydroxyphenylalanine containing decapeptide described above that represents a sequence from the MAPs of the mussel mytilis edulis. This decapeptide can be conjugated to different polymers in order to generate a biomimetic adhesive composition. The cross-linkage of DOPA groups to form the biomimetic adhesive composition analogous to the MAPs can be carried out enzymatically or oxidatively. However, the oxidative cross-linking leads to losses in adhesive strength. US 20030087338 therefore also describes oxidation-independent aggregation and/or gelation phenomena for producing corresponding polymers or copolymers. Polyethylene glycols or polyalkylene oxides are represented as possible polymers or copolymers. A combination with acrylate-containing adhesive compositions is not disclosed. The described decapeptide synthesis essential for the production of the biometic adhesive composition has furthermore proven to be complex and time-consuming.

The object of the present invention is to provide adhesive compositions, in particular acrylate adhesive compositions, which have a better adhesive strength compared to the prior art and are less moisture-sensitive. In particular, the object of the present invention is to provide an adhesive composition that can be combined with the principle of the waterproof adhesion of barnacles and mussels without the unfavorable circumstances and disadvantages of the decapeptide synthesis having to be taken into consideration.

SUMMARY OF THE INVENTION

Accordingly, the present invention provides an acrylate and/or methacrylate adhesive composition which comprises N-methacryloyl-3,4-dihydroxyphenylalanine and/or N-acryloyl-3,4-dihydroxyphenylalanine.

In one aspect, the composition may comprise from 5% by weight to 20% by weight, based on the total weight of the composition, of N-methacryloyl-3,4-dihydroxyphenylalanine and/or N-acryloyl-3,4-dihydroxyphenylalanine.

In another aspect, the composition may be a self-adhesive composition.

In yet another aspect, the composition may comprise at least one acrylate alkylacrylate copolymer. For example, the at least one acrylate alkylacrylate copolymer may comprise a copolymer of formula

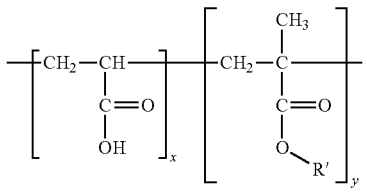

wherein R' represents a long-chain alkyl group and x and y represent stoichiometric ratios of the respective units.

The present invention also provides a method of producing a biocompatible acrylate adhesive composition. The method comprises combining N-methacryloyl-3,4-dihydroxyphenylalanine and/or N-acryloyl-3,4-dihydroxy-phenylalanine as monomers with an acrylate copolymer and/or a methacrylate copolymer.

In one aspect of the method, the acrylate copolymer and/or methacrylate copolymer may comprise at least one acrylate alkylacrylate copolymer.

The present invention also provides a combination of (i) N-acryloyl-3,4-dihydroxyphenylalanine and/or N-methacryloyl-3,4-dihydroxyphenyl-alanine and (ii) an acrylate polymer and/or a methacrylate polymer.

In one aspect, the combination may be suitable for producing a biomimetic adhesive composition.

The present invention also provides a self-adhesive dressing or plaster which comprises the adhesive composition of the present invention set forth above (including the various aspects thereof).

The present invention also provides a method of adhering substrates under moist conditions. The method comprises adhering the substrate with the adhesive composition of the present invention set forth above (including the various aspects thereof).

The present invention also provides a method of adhering a substrate to human skin. The method comprises using a substrate which comprises the adhesive composition of the present invention set forth above (including the various aspects thereof).

In one aspect of the method, the substrate may comprise at least one of a patch, a pad, a tape, a wipe, a binding, a plaster, a dressing, a cataplasm, a bandage and a mask.

DETAILED DESCRIPTION OF THE INVENTION

It was surprising and extremely astonishing to one skilled in the art that an acrylate adhesive composition comprising N-methacryloyl-3,4-dihydroxyphenylalanine and/or N-acrylol-3,4-dihydroxyphenylalanine attains the set objects.

B. P. Lee et al. described a DOPA-containing monomer, N-methacryloyl-3,4-dihydroxyphenylalanine for the first time in his publication—J. Biomater. Sci. Polymer Edn. 15, 449-464 [2004].

After exhaustive testing, with the aid of this monomer it has now been rendered possible according to the invention to dispense with the complex method of decapeptide synthesis, as described in the prior art.

It has surprisingly been shown that this monomer, N-methacryloyl-3,4-dihydroxyphenylalanine, like the N-acrylol-3,4-dihydroxyphenylalanine, which can be produced in an analogous manner, can be directly used as additional starting material in the polymerization approaches for acrylate adhesive compositions without them losing their positive properties of a waterproof adhesion. This is made possible since the subsequent polymerization of the monomers and the acrylates is not carried out via the DOPA itself, but via the acryloyl or methacryloyl part of the respective monomer, and—this is the core of the invention—complex enzymatic, oxidative or other mechanisms for forming the final adhesive polymer are therefore not necessary.

In this manner N-acrylol-3,4-dihydroxyphenylalanine and/or N-methacryloyl-3,4-dihydroxyphenylalanine can be incorporated in standard blends of acrylic acid and acrylic esters and then lead to waterproof, MAP-analogous adhesions of the adhesive compositions.

However, compared to the known MAP adhesions of the prior art, it has been possible for the first time to impart waterproof adhesive properties to an acrylate adhesive substance in this form and moreover to dispense with complicated, time-consuming process steps that impair the adhesive properties, such as decapeptide synthesis, in the production.

It is advantageous to use contents of N-acrylol-3,4-dihydroxyphenylalanine and/or N-methacryloyl-3,4-dihydroxyphenylalanine between 5% by weight and 20% by weight based on the total adhesive composition.

The production of N-acrylol-3,4-dihydroxyphenylalanine and N-methacryloyl-3,4-dihydroxyphenylalanine is carried out according to the instructions from J. Biomater. Sci. Polymer Edn. 15, 449-464 [2004], the disclosure of which is hereby incorporated into the content of the present invention in its entirety.

Although acrylate-based adhesive compositions as a rule have a good permeability for water vapor, their adhesive performance is more moderate.

The use of skin-friendly adhesive compositions, such as acrylate adhesive compositions, is not always worth considering because of the low shear stability and contact stickiness. An improvement through an aftertreatment, in particular cross-linking, is possible, but the result always remains unsatisfactory. Furthermore, the adhesive strength on the carrier reverse side of such systems is not sufficient for a stable functional bandage in the case of bandages of several layers applied in a circular manner. The proprioreceptive effect is also lower with respect to the systems with a zinc-rubber adhesive composition.

Other known adhesive systems based on conventional block copolymers on the one hand are not skin-friendly due to a high addition of stabilizers or have hitherto shown only a suitability for technical applications due to the high cohesiveness, on the other hand they cannot be adjusted to strongly stick or adhere to the skin.

The cited adhesive compositions, acrylate and methacrylate adhesive compositions, are among the pressure-sensitive self-adhesive compositions, wherein the compositions can be present in a carrier matrix for the processing. Customary organic or inorganic solvents or dispersing agents are understood to be a carrier matrix.

A polymer matrix of hydrophilic polymers, such as, e.g., acrylates, polyvinyl pyrrolidone/polyacrylic acid or polyacrylic acid/polyvinyl alcohol can be used as a preferred matrix.

Polyacrylates that are advantageous according to the invention are acrylate-alkylacrylate copolymers, in particular those selected from the group of so-called carbomers or carbopols (Carbopol® is actually a registered trademark of B.F. Goodrich Company). In particular the acrylate alkylacrylate copolymers that are advantageous according to the invention are characterized by the following structure:

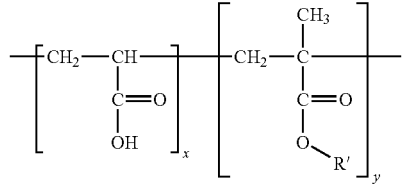

R' therein represents a long-chain alkyl radical and x and y numbers that symbolize the respective stoichiometric proportion of the respective comonomers.

Acrylate copolymers and/or acrylate alkylacrylate copolymers are particularly preferred according to the invention which are available from B.F. Goodrich Company under the trade names Carbopol® 1382, Carbopol® 981 and Carbopol® 5984, preferably polyacrylates from the group of Carbopols of the types 980, 981, 1382, 2984, 5984 and in particular preferred Carbomer 2001.

N-Acrylol-3,4-dihydroxyphenylalanine and/or N-methacryloyl-3,4-dihydroxy-phenylalanine monomers are added to these acrylate or methacrylate polymers or copolymers during the production of the adhesive composition.

Adhesive compositions are thereby obtained that on the one hand have the advantages of the acrylate adhesive compositions and on the other hand do not exhibit any loss of adhesive strength even under the influence of moisture. The combination of N-acrylol-3,4-dihydroxyphenylalanine and/or N-methacryloyl-3,4-dihydroxyphenyl-alanine and acrylate or methacrylate polymers thus renders possible the production of biomimetic adhesive compositions.

The decapeptide synthesis, i.e., the cross-linking analogous to the MAPs of DOPA groups to a biomimetic adhesive composition in an enzymatic or oxidative manner, which is disadvantageous, as has been described, is preferably omitted in the production.

The biomimetic acrylate adhesive composition as an adhesive composition in dressings or plasters makes it possible to provide dressings or plasters that also guarantee a sufficiently firm adhesion, in particular to human skin, even under water or moist conditions. The problems in plaster adhesion to human skin that commonly occur when sweating, when washing, in the rain or other damp influences are thus solved.

In addition to the adhesive compositions, plasters sometimes also contain a carrier material on which the adhesive composition is applied.

All rigid and elastic sheet materials of synthetic and natural raw materials are suitable as carrier materials. Carrier materials are preferred that can be used after application of the adhesive substance such that they fulfill properties of a functionally appropriate dressing. Textiles such as woven fabrics, knitted fabrics, layered fabrics, non-woven fabrics, laminates, nets, foils, foams and papers are listed by way of example. Furthermore, these materials can be pre-treated or post-treated. Standard pre-treatments are corona and hydrophobization; conventional post-treatments are calendering, tempering, coating, stamping and covering.

The carrier materials preferably comprise an air-permeable and water vapor-permeable but water-impervious polymer layer with a thickness of approx. 10 to 100 μm. The possibly flexible carrier foil preferably comprises polymers of polyurethane, PE, PP, polyamide, polyester or polyether ester or known carrier materials such as woven fabrics, non-woven fabrics, foams, plastics, etc.

The adhesive matrix according to the invention can be applied to this carrier layer or carrier foil, as is known from the prior art. The matrix is thereby covered with the carrier material on one side and applied as a composite foil. Depending on the carrier material used, the water vapor-permeability, the strength of the wound covering, the padding against pressure and other physical properties of the wound covering can be thereby controlled.

The bandage material according to the invention is then built up according to known wound bandages. They generally comprise a carrier material that is provided on one side with a self-adhesive layer, the adhesive composition according to the invention. A dressing is then applied to this self-adhesive coating. In order to guarantee easy handling, the self-adhesive coating is furthermore covered with a protective layer, e.g., a sealing paper.

Finally, the carrier material equipped to be self-adhesive after the application can additionally be covered or provided with a dressing, padding.

In addition to the use as a plaster, e.g., a less adhesive patch or pad can also be equipped with the adhesive composition according to the invention, wherein the adhesive strength can be specifically adjusted according to the respective purpose.

The terms plaster, cosmetic/dermatological matrices and cosmetic/dermatological pads are used here in a synonymous manner, just as all cosmetically applicable dressings such as patch, pad, tapes, wipes, bindings, plasters, dressings, cataplasm, bandages and/or masks are understood with the dressing according to the invention.

The adhesive composition according to the invention has made it possible for the first time to ensure an adhesion of substrates under damp conditions, in particular a biocompatible and waterproof adhesion on human skin.

What is claimed is:

1. An acrylate and/or methacrylate adhesive composition, wherein the composition comprises at least one of N-methacryloyl-3,4-dihydroxyphenylalanine and N-acryloyl-3,4-dihydroxyphenylalanine.

2. The composition of claim 1, wherein the composition comprises from 5% by weight to 20% by weight, based on a total weight of the composition, of at least one of N-methacryloyl-3,4-dihydroxyphenylalanine and N-acryloyl-3,4-dihydroxyphenylalanine.

3. The composition of claim 1, wherein the composition is a self-adhesive composition.

4. The composition of claim 1, wherein the composition comprises at least one acrylate alkylacrylate copolymer.

5. The composition of claim 4, wherein the at least one acrylate alkylacrylate copolymer comprises a copolymer of formula

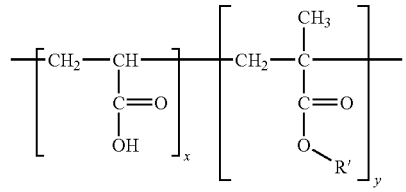

wherein R' represents a long-chain alkyl group and x and y represent stoichiometric ratios of the respective units.

6. A self-adhesive dressing or plaster, wherein the dressing or plaster comprises the composition of claim 1.

7. A method of adhering substrates under moist conditions, wherein the method comprises adhering the substrate with the composition of claim 1.

8. A method of adhering a substrate to human skin, wherein the method comprises using a substrate which comprises a composition of claim 1.

9. The method of claim 8, wherein the substrate comprises at least one of a patch, a pad, a tape, a wipe, a binding, a plaster, a dressing, a cataplasm, a bandage and a mask.

10. A method of producing a biocompatible acrylate adhesive composition, wherein the method comprises combining at least one of N-methacryloyl-3,4-dihydroxyphenylalanine and N-acryloyl-3,4-dihydroxy-phenylalanine as monomers with at least one of an acrylate copolymer and a methacrylate copolymer.

11. The method of claim 10, wherein the at least one of an acrylate copolymer and a methacrylate copolymer comprises at least one acrylate alkylacrylate copolymer.

12. A combination of (i) at least one of N-acryloyl-3,4-dihydroxyphenylalanine and N-methacryloyl-3,4-dihydroxyphenylalanine and (ii) at least one of an acrylate polymer and a methacrylate polymer.

13. The combination of claim 12, wherein the combination is suitable for producing a biomimetic adhesive composition.

* * * * *